(12) United States Patent
Pan

(10) Patent No.: US 7,749,166 B2
(45) Date of Patent: Jul. 6, 2010

(54) SYSTEM AND METHOD FOR FILTERING IN IMAGING SYSTEMS

(75) Inventor: Lihong Pan, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 1413 days.

(21) Appl. No.: 10/832,052

(22) Filed: Apr. 26, 2004

(65) Prior Publication Data
US 2005/0251008 A1    Nov. 10, 2005

(51) Int. Cl.
*A61B 8/06* (2006.01)
(52) U.S. Cl. ...................................... 600/455
(58) Field of Classification Search ......... 600/440–443, 600/446, 453–457; 382/260; 128/916; 73/861.25
See application file for complete search history.

(56) References Cited

U.S. PATENT DOCUMENTS

| | | | |
|---|---|---|---|
| 5,269,308 A | 12/1993 | Hagiwara et al. | |
| 5,383,464 A | 1/1995 | Shiba | |
| 5,443,071 A | 8/1995 | Banjanin et al. | |
| 5,544,659 A | 8/1996 | Banjanin | |
| 5,910,118 A | 6/1999 | Kanda et al. | |
| 6,146,331 A * | 11/2000 | Wong | 600/454 |
| 6,210,332 B1 * | 4/2001 | Chiao et al. | 600/443 |
| 6,210,334 B1 | 4/2001 | Phillips | |
| 6,277,075 B1 * | 8/2001 | Torp et al. | 600/443 |
| 6,296,612 B1 | 10/2001 | Mo et al. | |
| 6,530,885 B1 * | 3/2003 | Entrekin et al. | 600/437 |

OTHER PUBLICATIONS

A.P.G. Hoeks, et al "An Efficient Algorithm to Remove Low Frequency Doppler Signals in Digital Doppler Systems", Ultrasonic Imaging 13, 135-144 (1991).
S. Bjaerum, et al. "Clutter Filter Design for Ultrasound Color Flow Imaging", IEEE Transactions on Ultrasonics, Perroelectrics and Frequency Control, vol. 49, No. 2, Feb. 2002.

* cited by examiner

*Primary Examiner*—Brian Casler
*Assistant Examiner*—Elmer Chao
(74) *Attorney, Agent, or Firm*—Dean Small; Small Patent Law Group (57) ABSTRACT

Systems and methods for signal filtering are provided. A signal filter includes a linear regression filter component and a finite impulse response filter component. A received signal is first filtered by the linear regression filter component and then filtered by the finite impulse response filter component.

24 Claims, 8 Drawing Sheets

SYSTEM AND METHOD FOR FILTERING IN IMAGING SYSTEMS

BACKGROUND OF THE INVENTION

This invention relates generally to systems for filtering signals, and more particularly, to systems for filtering signals, especially signals received in medical imaging systems.

Ultrasound imaging is used in a variety of clinical settings, including, for example, obstetrics, gynecology, cardiology and oncology. Ultrasound imaging is widely used to study anatomical structures, detect anomalies in tissues and measure blood flow within the body. In ultrasound imaging systems, a transducer probe of an ultrasound machine generates and transmits acoustic waves and receives the echoes reflected, for example, by a body or portion thereof.

Doppler ultrasound, which is based upon the Doppler effect, is used for measuring the rate of blood flow through the human body, for example, through the heart, major arteries and veins in the body. In accordance with the Doppler effect, the frequency of reflected echoes from a moving object are different from the frequency of the transmitted waves. The frequency of the echoes is higher than that of the transmitted waves if the object is moving towards the probe and vice versa.

Doppler ultrasound measures the change in frequency of the echoes to calculate the flow velocity of a body fluid such as blood. The velocity of blood is not same throughout the flow region, for example, through the blood vessels carrying the blood. Typically, the velocity follows a parabolic profile, being highest at the center of the blood vessels and decreasing towards the walls of the vessels. Signals originating from the stationary and slow moving tissues, such as vessel walls, have a lower Doppler frequency shift. The vessel wall signal is typically 40 to 100 db stronger than the signal from the blood. Without sufficient wall signal rejection, low velocity blood flow cannot be measured or detected.

Ultrasound systems use a high pass filter, sometimes referred to as a vessel wall filter, to remove the low frequency tissue motion signal in blood flow velocity estimations. When both B-mode image and flow image, including spectral Doppler imaging and color flow imaging, are active, ultrasound systems transmit acoustic waves alternatively for flow imaging and B mode imaging. The vessel wall filter is turned on in each flow segment. The abrupt turn-on at the beginning of each Doppler segment may introduce transient noise. The transient noise obscures the low amplitude Doppler signal from the blood flow, which can cause difficulty for some diagnoses based on velocity measurements. This transient noise also may corrupt the mean velocity estimation in color flow imaging. It is very important for the wall filter to efficiently remove the low frequency tissue motion signal without introducing transient noise in Doppler frequency estimation.

Currently, Infinite Impulse Response (IIR) filters and Finite Impulse Response (FIR) filters are used to remove these low frequency signals. IIR filters can provide sharper roll-offs at cutoff frequencies with fewer sample points. However, these IIR filters may introduce large transient artifacts. The artificial signals shift to higher frequency with higher cutoff. Further, FIR filters require a long filter length to achieve sharp roll-offs. However, the sample points limit the actual filter length in the case of FIR filters. Because of the slow roll-off, the attenuation may not be adequate to remove the much stronger low velocity tissue motion signal for a lower cutoff filter. In addition, the higher cutoff filter may remove too much of the blood flow signals. FIR filters also may introduce transient noise that may be observed as multiple narrow frequency bands spreading from the baseline into higher frequencies. These transient noises are stronger with stronger tissue wall signals. Thus, the transient signals and the tissue wall signals obscure or interfere with the actual low frequency flow signals and may cause the flow signals to be undetectable. This also may result in inaccurate mean velocity estimation.

Thus, known ultrasound filters may not provide efficient removal of low frequency tissue motion signals and result in some transient noises. These filters may also obscure or interfere with the detection of low velocity flow both in Doppler spectral waveform and color flow imaging.

BRIEF DESCRIPTION OF THE INVENTION

In one embodiment, a signal filter is provided. The signal filter includes a linear regression filter component and a finite impulse response filter component, with a received signal first filtered by the linear regression filter component and then filtered by the finite impulse response filter component.

In another embodiment, a method for filtering signals from a medical imaging system is provided. The method includes receiving signals from a medical imaging system, filtering the received signals using a linear regression filter, and filtering signals filtered by the linear regression filter using a finite impulse response filter.

DETAILED DESCRIPTION OF THE INVENTION

Various embodiments of the present invention provide systems and methods for filtering signals, especially low frequency signals reflected from body parts during medical imaging, including filtering low frequency tissue motion signals that are reflected by vessel walls carrying body fluids (e.g., blood).

Figure 1:
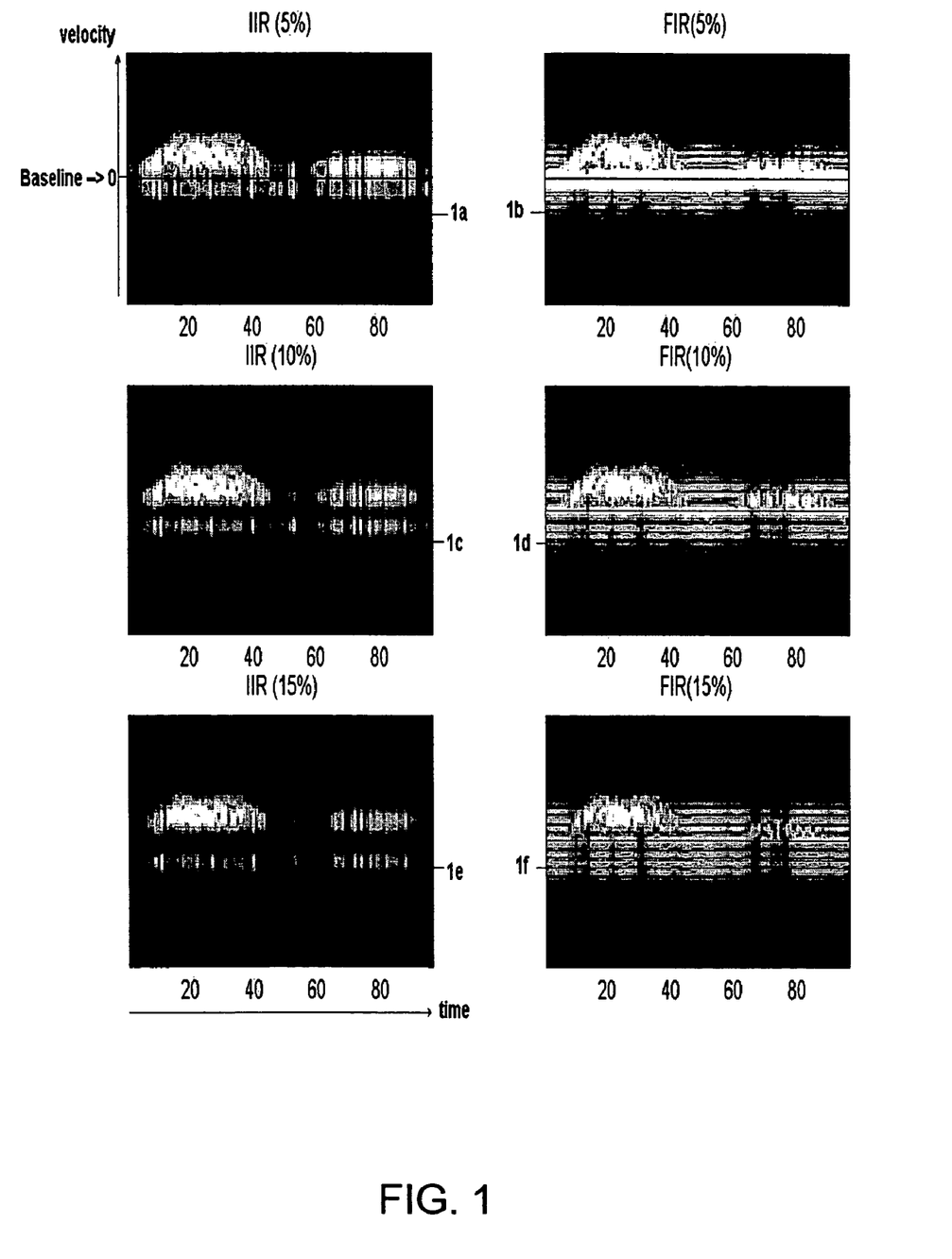
FIG. 1 shows prior art Doppler spectral waveforms for a flow using IIR and FIR high pass filters.

FIG. 1 shows Doppler spectral waveforms of a flow with Infinite Impulse Response (IIR) and Finite Impulse Response (FIR) high pass filters at different cut-off frequencies. The waveforms from the IIR and FIR filters have cutoff frequencies of 5%, 10% and 15% of the Nyquist frequency. IIR filters can provide sharper roll-offs at cutoff frequencies with fewer sample points. However, IIR filters may introduce large transient artifacts. These artifacts are shown in the figures as low frequency band noise above and below the baseline as seen in the spectra from IIR filter with 10% cut-off. The artificial signals shift to higher frequencies with higher cutoffs.

FIR filters require a long filter length to achieve sharp roll-offs. However, the filter length is limited by the sample points. In FIG. 1, the FIR filter length is thirty-one taps, a tap being a coefficient/delay pair in a filter as is known. Because of the slow roll-off, the attenuation around DC (baseline) may not be adequate to remove the much stronger low velocity tissue motion signal for a lower cutoff filter as seen in the spectra from FIR filter with 5% cut-off. Moreover, the higher cutoff filter may remove too much of the blood flow signals. The frequency band around DC with a 5% cutoff FIR filter is the tissue motion signal remaining after FIR filtering. The spectra with FIR filters also show some transient noise as multiple narrow frequency bands spreading from the baseline into higher frequencies, as seen in the spectra of FIR filter with 15% cut-off. These transient noises are stronger with stronger tissue wall signals. The transient signals and the tissue wall signals may obscure or interfere with the actual low frequency flow signals and make these signals undetectable. These transient signals may also make the mean velocity estimation inaccurate.

Figure 2:
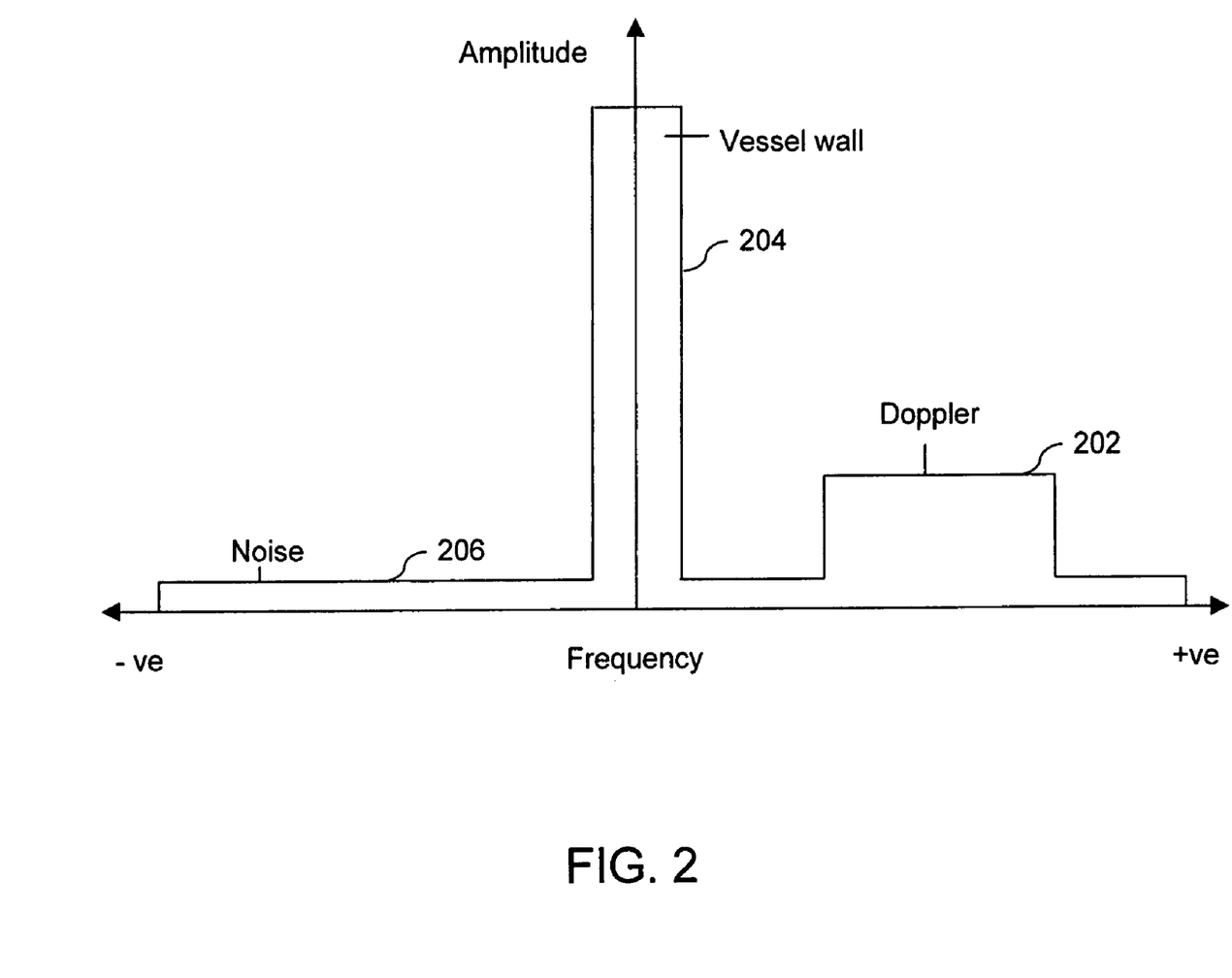
FIG. 2 is a signal diagram showing different types of signals reflected from an object under examination during Doppler ultrasound imaging and the noise component introduced during filtering.

FIG. 2 is a signal diagram showing different types of signals reflected from an object under examination during Doppler ultrasound imaging before filleting is performed. Doppler signal 202 is the desired signal to be used for plotting the waveform. Vessel wall signal 204 is the high amplitude, low frequency signal that needs to be filtered. Noise 206 is the background noise.

Figure 3:
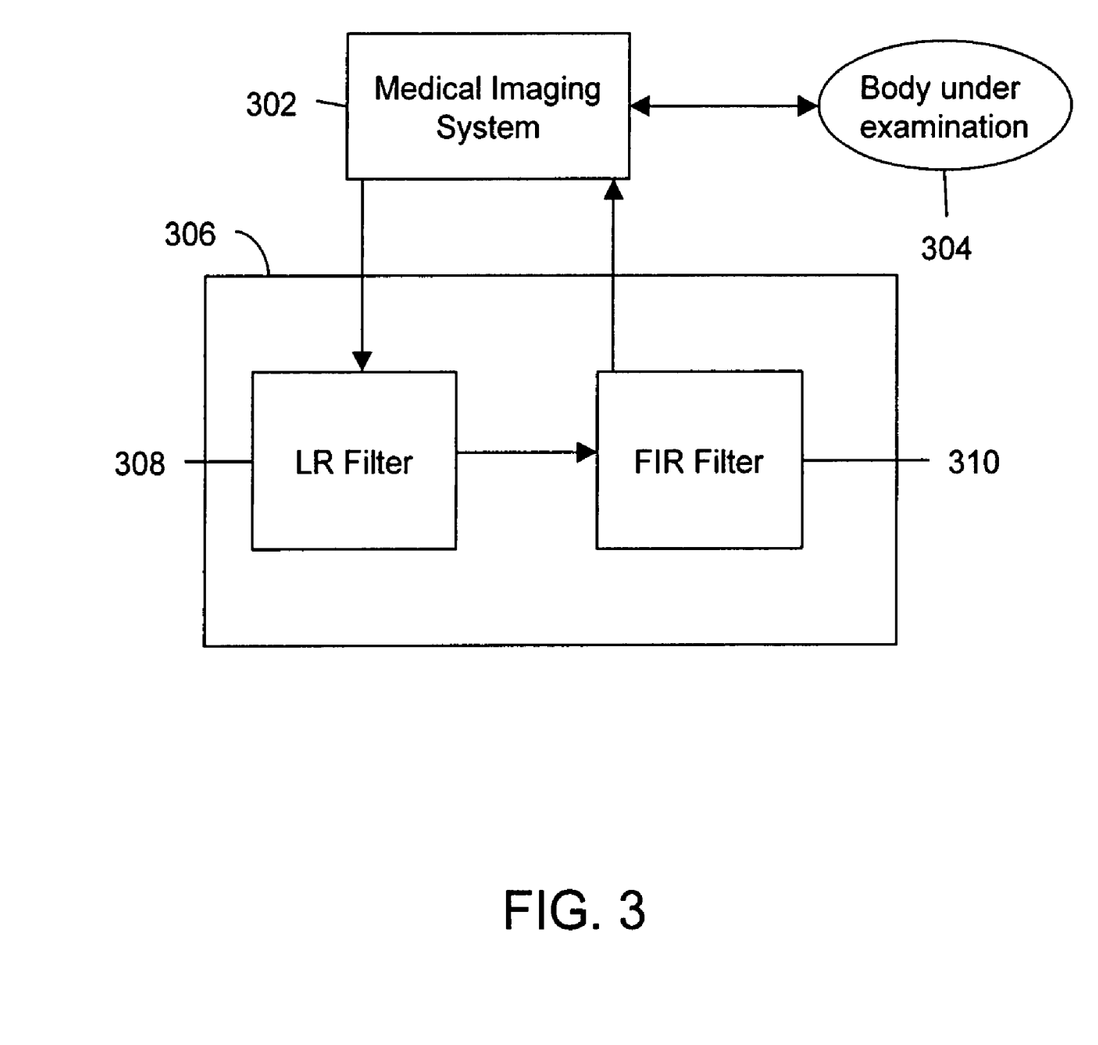
FIG. 3 is a block diagram showing an image filtering system in accordance with an exemplary embodiment of the present invention.

FIG. 3 is a block diagram showing an image filtering system in accordance with an exemplary embodiment of the present invention. Specifically, a medical imaging system 302, such as an ultrasound machine or scanner, is used, for example, to generate and transmit acoustic waves inside a body 304 under examination. These acoustic waves are reflected by objects within body 304 under examination. The reflected echoes are received by medical imaging system 302. Upon analysis, the signals may be transformed into moving images corresponding to, for example, an organ, tissue or body fluid being examined. The signals may contain low frequency wall signals as described herein, and which are undesirable. These undesirable signals or signal components are removed with a signal filter 306 having a linear regression (LR) filter component 308 and a finite impulse response (FIR) filter component 310. In one embodiment, both LR and FIR filter components 308 and 310 are high pass filters. It should be noted that the filter components may be constructed or provided as any type of filters or filtering components as needed or desired. For example, the filter components can be configured by varying the FIR filter length and the cut-off frequency.

Figure 4:
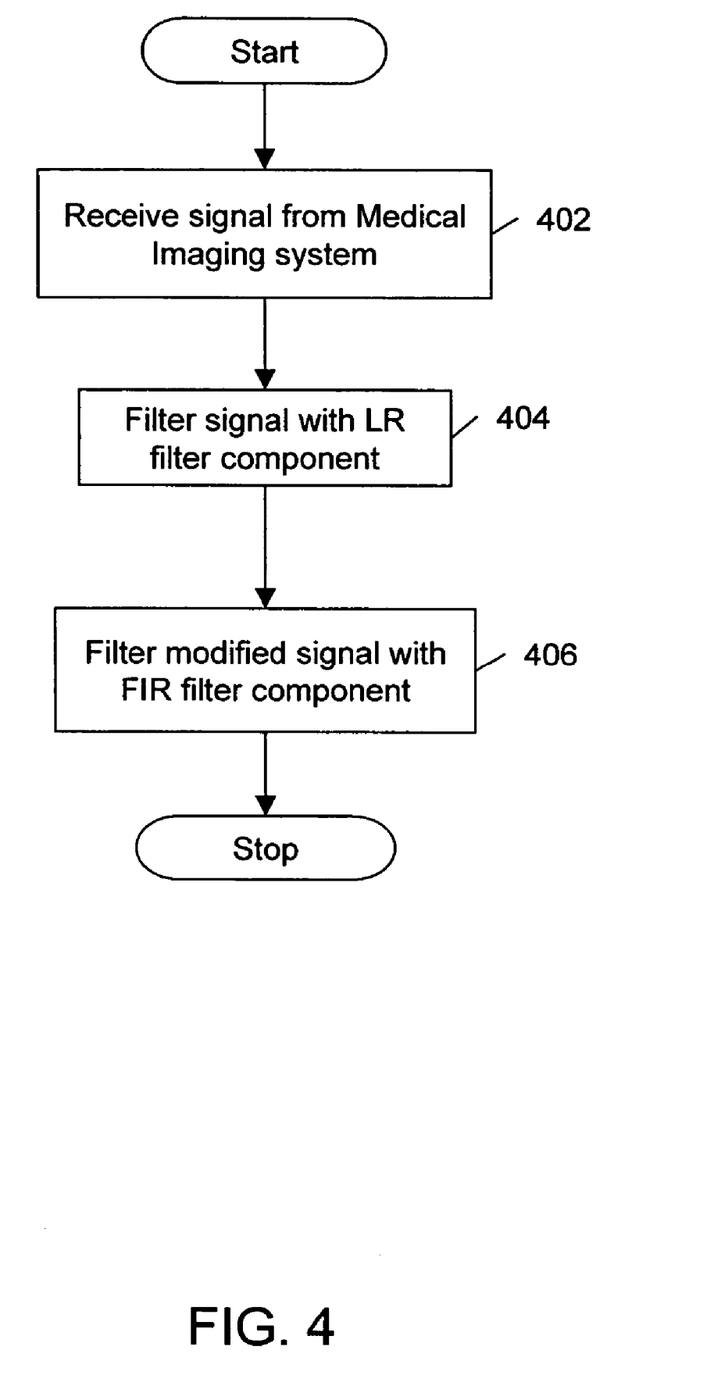
FIG. 4 is a flowchart illustrating a filtering process in accordance with an exemplary embodiment of the present invention.

FIG. 4 is a flowchart illustrating a filtering process in accordance with an exemplary embodiment of the present invention. At 402, imaging system 302 transmits acoustic waves inside, for example, a human body. An acoustic wave travels through the body tissue until it hits an object, obstruction or other interface, which may be where two different tissues are contiguous. This interface may cause some of the sound waves to be reflected back while others to continue to travel through to the next tissue. Echoes are received by imaging system 302 and converted into electric pulses. The electric pulses are then provided to a computer/display after signal processing, to form, for example, moving images of the organs or tissue being examined. These received signals also include low frequency signals arising from the vessel walls and slow moving tissues.

In various embodiments, the signals are filtered by an LR filter component 308 at 404 to remove these low frequency signals. The signals are best fit to a linear curve and the linear curve is then subtracted from the signals to remove, for example, vessel wall signals in a medical imaging application. This is referred to as 'first order LR filtering'. In another embodiment of the present invention, for example, where the wall signals are not very strong due to detection of the signal at the center of a large vessel, the mean of the signal is subtracted from the signal to remove the wall signal. This is referred to as 'zero order LR filtering'. LR filter component 308 filters and removes the wall signal around the baseline.

The signal filtered with LR filter component 308 is further filtered with FIR filter component 310 at 406 if further filtering is desired. A cut-off frequency may be specified for FIR filter component 310 and all the signals below the specified cut-off are removed from the signals received by the FIR filter component 310. The cut-off frequency is a percentage of the Nyquist frequency and can be changed by adjusting the filtering level of FIR filter component 310 as is known. The value of the cut-off may vary with the nature or type of the signal to be filtered or the particular application. For example, if high frequency flow is to be analyzed or if the tissue signal is strong, a higher cut-off percentage is provided. If signals from fluid flow across the baseline are to be analyzed, a low percentage cut-off is provided.

In various embodiments, LR filter component 308 and FIR filter component 310 are configured to filter signals received from objects within human body 304. For example, the filters 308 and 310 may be configured to remove high-amplitude, low-velocity signals from vessel walls or to remove signals from slow moving tissues and allow signals from moving fluid to pass. The signal filter 306 is configurable for operation in connection with different imaging systems. It should be noted that the configuration of the filters as described herein is only exemplary in nature and in no way intended to limit the scope of the various embodiments, which may be implemented using other configurations for the filters or different types of filters.

Further, the configuration of the FIR filter component 310 may be based upon numerous factors, such as, for example, the object within a human body being imaged, the blood vessels being imaged and the imaging procedure to be performed. The filter configuration may be changed, for example, depending on the signal length in each flow transmit segment.

Figure 5:
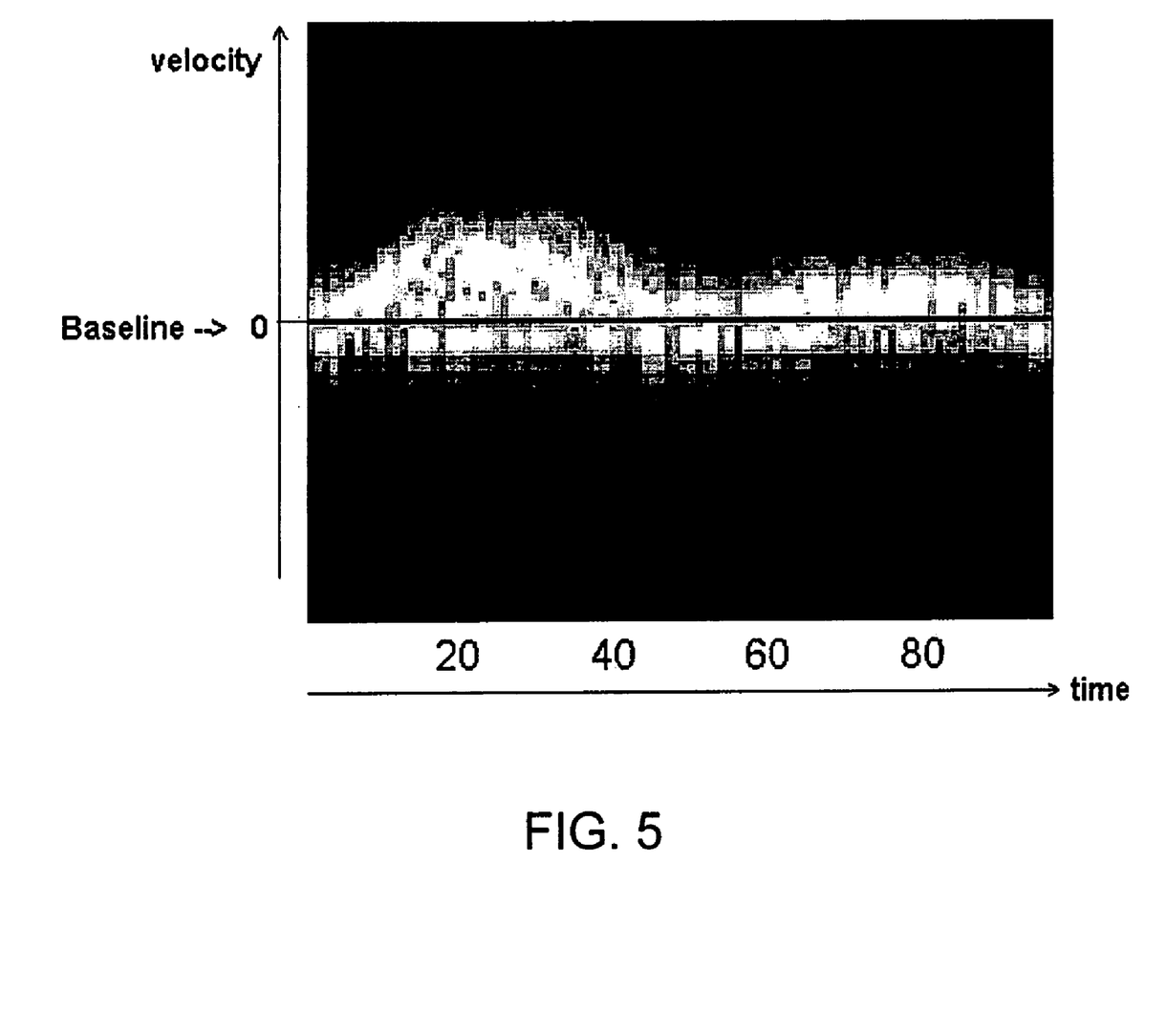
FIG. 5 is an exemplary spectral Doppler waveform produced with zero order LR filtering of signals in accordance with an exemplary embodiment of the present invention.

FIG. 5 shows an exemplary spectral Doppler waveform produced using zero order LR filtering of signals in accordance with various embodiments of the present invention. Zero order LR filtering is effective, for example, when the wall signals are weak. As shown in the figure, the low frequency signals around the baseline are present even after zero order LR filtering because the wall signals are strong. In such a case, first order LR filtering may be used.

Figure 6:
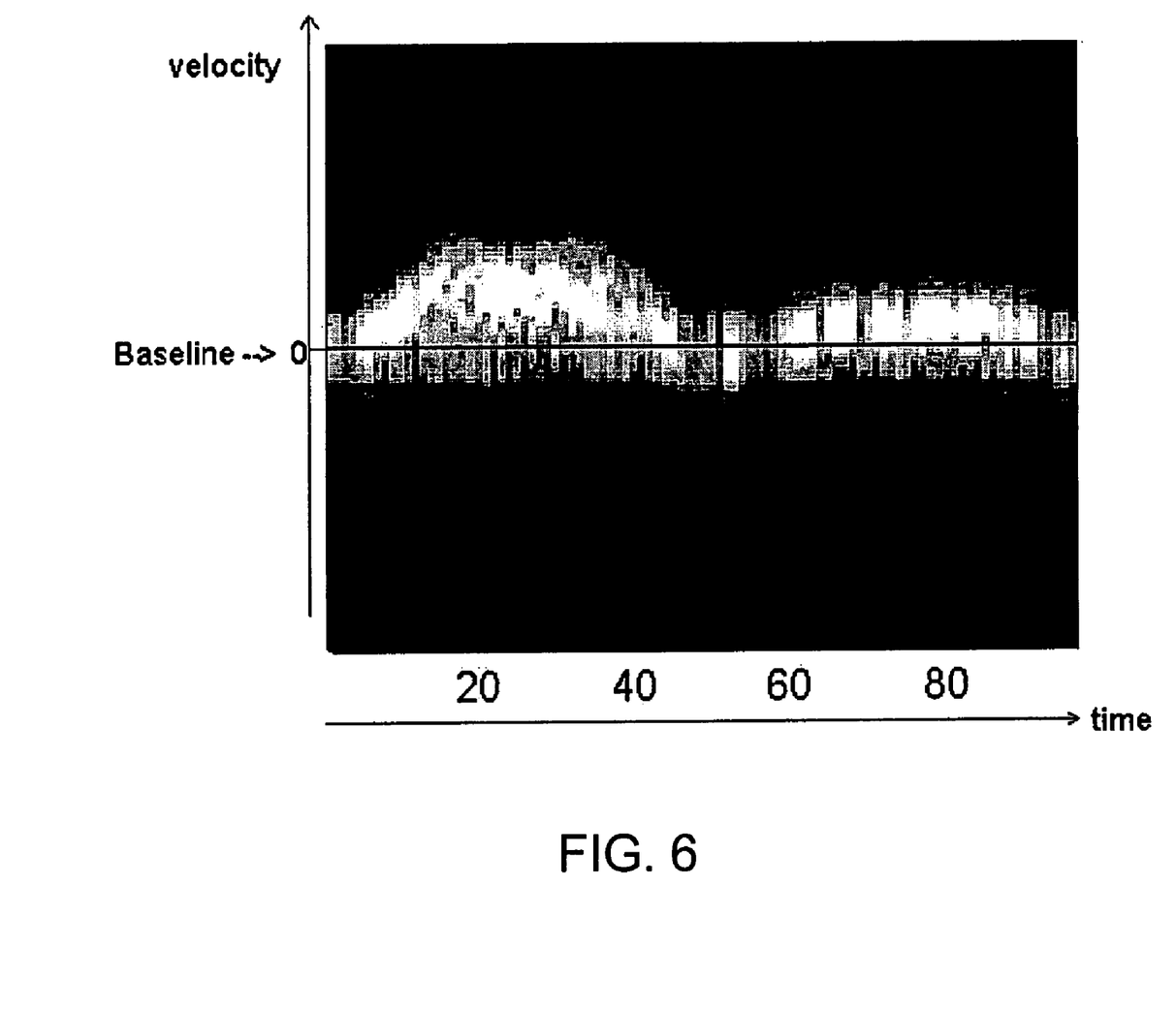
FIG. 6 is an exemplary spectral Doppler waveform produced with first order LR filtering of signals in accordance with an exemplary embodiment of the present invention.

FIG. 6 shows an exemplary spectral Doppler waveform produced using first order LR filtering of signals in accordance with various embodiments of the present invention. As shown in the figure, first order LR filtering is more effective than zero order LR filtering in filtering low frequency signals.

The low frequency component remaining in the signal after first order LR filtering is weak, as shown around the baseline in FIG. 6.

Figure 7:
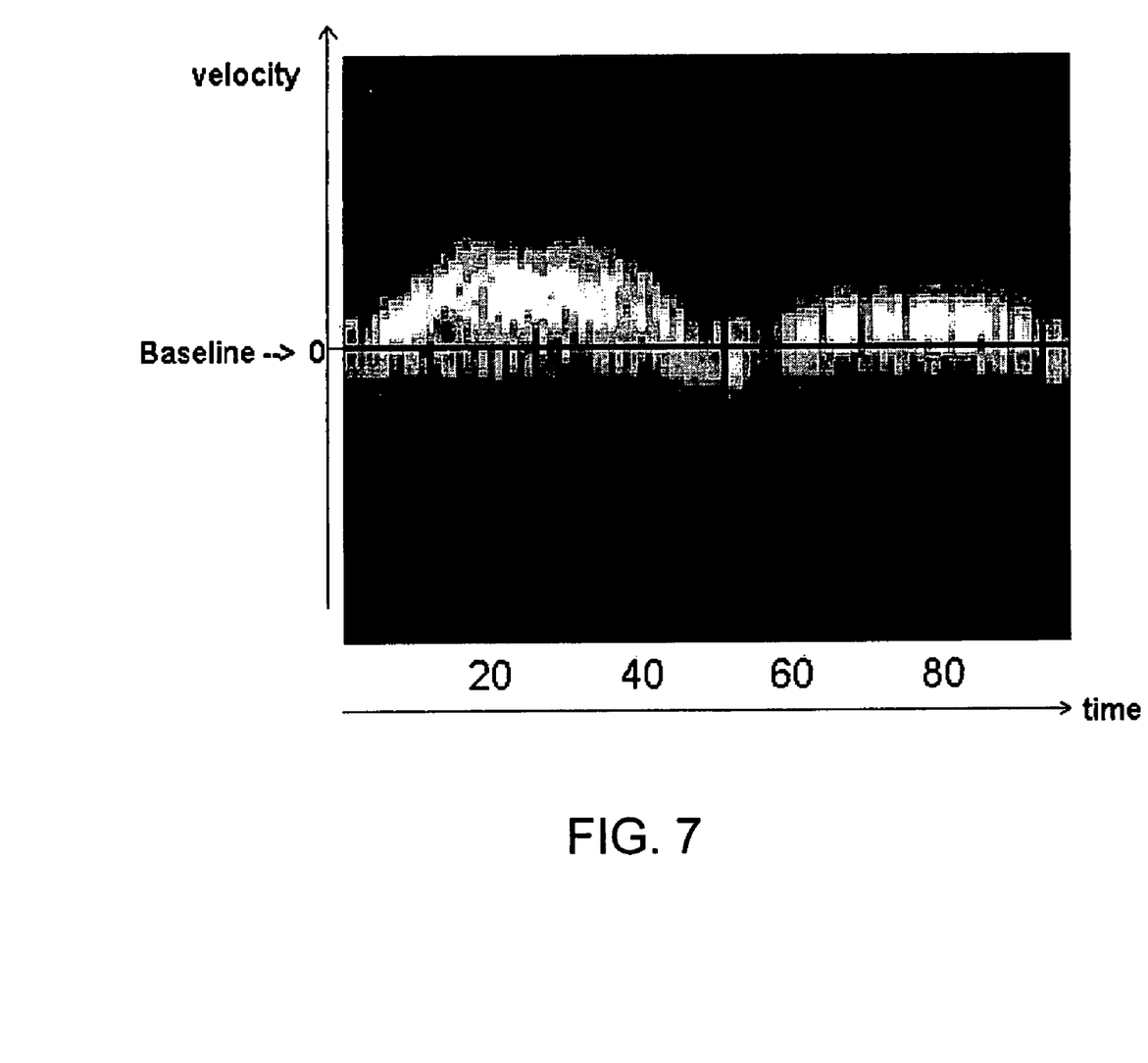
FIG. 7 is an exemplary spectral Doppler waveform produced with combined LR and FIR filtering with a 5% cut off in accordance with an exemplary embodiment of the present invention.

FIG. 7 shows an exemplary spectral Doppler waveform produced using combined LR and FIR filtering with a 5% cutoff in accordance with various embodiments of the present invention. Low frequency signals or additional low frequency signals are filtered by FIR filtering after LR filtering as described herein.

Figure 8:
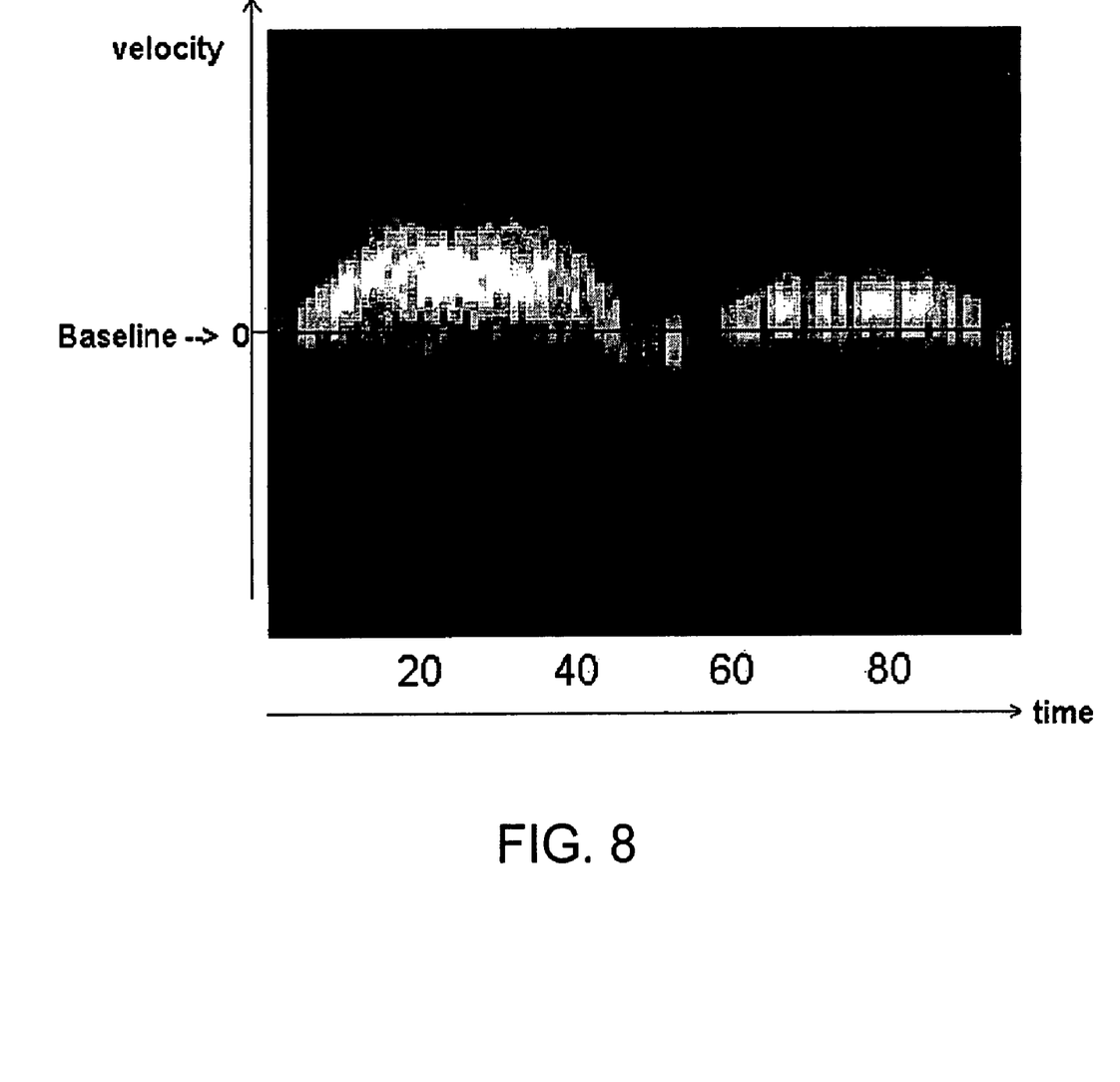
FIG. 8 is an exemplary spectral Doppler waveform produced with combined LR and FIR filtering with a 10% cutoff in accordance with an exemplary embodiment of the present invention.

FIG. 8 shows an exemplary spectral Doppler waveform produced using combined LR and FIR filtering with a 10% cutoff in accordance with various embodiments of the present invention. In comparison to FIG. 7, more low frequency signal is removed at the higher cut-off value. As shown in FIG. 8 the low velocity flow below the baseline becomes clear. Most of the low frequency signal is filtered after this stage of filtering. The band of low frequency signals around the baseline is negligible after this stage.

Various embodiments of the present invention provide a combination of LR and FIR filter components for filtering low frequency tissue motion signals. The filter combination also minimizes the transient noise while providing desired filtering. The filtering allows accurate mean velocity estimation in color flow imaging. Further, the filtering improves the detection of low velocity flow both in Doppler spectral waveform and color flow imaging. The accurate measurements of flow velocity results in accurate flow velocity related diagnosis.

It should be noted that various embodiments of the present invention may be implemented or embodied in the form of a computer system. Examples of a computer system include a general-purpose computer, a programmed microprocessor, a micro-controller, a peripheral integrated circuit element, and other devices or arrangements of devices that are capable of implementing the various embodiments of the present invention.

The computer system may include, for example, a computer, an input device, a display unit and an interface, for example, for accessing the Internet. The computer may include a microprocessor. The microprocessor may be connected to a communication bus. The computer also may include a memory. The memory may include Random Access Memory (RAM) and Read Only Memory (ROM). The computer system further may include a storage device, which may be a hard disk drive or a removable storage drive such as a floppy disk drive, optical disk drive and the like. The storage device also can be other similar means for loading computer programs or other instructions into the computer system.

The computer system executes a set of instructions that are stored in one or more storage elements, in order to process input data. The storage elements may also hold data or other information as desired. The storage element may be in the form of an information source or a physical memory element within the processing machine.

The set of instructions may include various commands that instruct the processing machine to perform specific tasks such as the methods of various embodiments of the present invention. The set of instructions may be in the form of a software program. The software may be in various forms such as, for example, system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

While the invention has been described in terms of various specific embodiments, those skilled in the art will recognize that the invention can be practiced with modification within the spirit and scope of the claims.

What is claimed is:

1. A signal filter for medical imaging, the signal filter comprising:
   a linear regression filter component comprising a tissue motion signal filter; and
   a finite impulse response filter component having an input connected to an output of the tissue motion signal filter, received signals first filtered by the linear regression filter component and then filtered by the finite impulse response filter component, wherein the linear regression filter component and the finite impulse response filter component are connected to a medical imaging system that comprises an ultrasound system and each of the linear regression filter component and the finite impulse response filter component comprises a high pass filter, and together are configured to remove low frequency signals in at least one of color flow or Doppler spectral flow detections.

2. A signal filter in accordance with claim 1 wherein the components are configured to filter signals received from objects within a human body.

3. A signal filter in accordance with claim 1 wherein the linear regression filter component comprises one of a zero order linear regression filter and a first order linear regression filter.

4. A signal filter in accordance with claim 1 wherein the finite impulse response filter component is configured to provide adjustable frequency cutoff levels.

5. A signal filter in accordance with claim 1 wherein the finite impulse response filter component is configured to be adjustable to optimize filtering of the received signals based upon a fluid flow level.

6. A signal filter in accordance with claim 1 wherein the finite impulse response filter component is configured to provide filtering at different frequency cutoff levels based upon one of a characteristic or a property of an object being imaged by the medical imaging system providing the received signals.

7. A signal filter in accordance with claim 1 wherein the finite impulse response filter component is configured to provide filtering at different frequency cutoff levels based upon one of a type of or a characteristic of a blood vessel within a human body being imaged by the medical imaging system providing the received signals.

8. A signal filter in accordance with claim 1 wherein the finite impulse response filter component is configured to provide filtering at different frequency cutoff levels to produce an output signal based upon a medical imaging procedure performed by the medical imaging system providing the received signals.

9. A signal filter in accordance with claim 1 wherein the components are configured to provide a vessel wall filter for the ultrasound imaging system configured to filter tissue motion signals within a human body.

10. A signal filter in accordance with claim 1 wherein the components are configured to filter motion signals other than a desired motion signal.

11. A signal filter in accordance with claim 10 wherein the components are configured to filter based on an amplitude of the motion signals.

12. A signal filter in accordance with claim 1 wherein the tissue motion signal filter is configured to first filter one of low frequency tissue motion signals or vessel wall motion signals from the received signals, and the finite impulse response filter is configured to further filter the received signals to reduce transient noise.

13. A signal filter in accordance with claim 1 wherein the received signals are ultrasound signals received from the medical imaging system, and the tissue motion signal filter is configured to first filter low frequency motion signals from the received signals and the finite impulse response filter further filters the received signals to remove additional low frequency motion signals.

14. A signal filter for a medical imaging system, said signal filter comprising:
   a linear regression filter component comprising a tissue motion signal filter configured to filter signals received from a medical imaging system that comprises an ultrasound system; and
   a finite impulse response filter component having an output connected to an input of the tissue motion signal filter and configured to filter signals received from the linear regression filter component, each of the components comprising a high pass filter and together configured to filter received motion signals to provide a fluid flow signal from within an object being imaged by the medical imaging system to remove low frequency signals in at least one of color flow or Doppler spectral flow detections.

15. A signal filter in accordance with 14 wherein the components together are configured to filter low frequency tissue motion signals and minimize transient noise signals.

16. A signal filter in accordance with 14 wherein the components together are configured to filter vessel wall motion signals.

17. A signal filter in accordance with 14 wherein the finite impulse response filter component is configured to provide filtering operation at different levels based on an image scan to be performed by the medical imaging system.

18. A signal filter in accordance with 14 wherein the finite impulse response filter component is configured to provide filtering operation at different levels based on at least one characteristic of a portion of a human body being imaged by the medical imaging system.

19. A signal filter in accordance with 14 wherein the linear regression filter component is configured to perform at least one of zero order linear regression filtering and first order linear regression filtering.

20. A signal filter in accordance with 14 wherein the finite impulse response filter component is configured to filter at different frequency cutoff levels.

21. A method for filtering signals from a medical imaging system, said method comprising:
   receiving signals from a medical imaging system, wherein the medical imaging system comprises an ultrasound system;
   filtering the received signals using a linear regression filter comprising a tissue motion signal filter; and
   filtering signals filtered by the linear regression filter using a finite impulse response filter having an input connected to an output of the tissue motion signal filter, wherein each of the linear regression filter and the finite impulse response filter comprises a high pass filter, and wherein the filtering removes low frequency signals in at least one of color flow or Doppler spectral flow detections.

22. A method in accordance with claim 21 wherein the filtering using the linear regression filter comprise one of a zero order linear regression filtering and a first order linear regression filtering.

23. A method in accordance with claim 21 wherein the filtering using the finite impulse response filter comprises adjusting the filtering level based on a percentage cutoff value.

24. A method in accordance with claim 23 wherein the percentage cutoff value is determined based on a scan to be performed by the medical imaging system.

* * * * *